(12) United States Patent
Constantine et al.

(10) Patent No.: US 7,074,425 B2
(45) Date of Patent: Jul. 11, 2006

(54) HEMOSTATIC COMPOSITIONS AND METHODS

(75) Inventors: Barry E. Constantine, Island Heights, NJ (US); Nels J. Lauritzen, Piscataway, NJ (US)

(73) Assignee: Bonewax, LLC, Princeton, NJ (US)

( * ) Notice: Subject to any disclaimer, the term of this patent is extended or adjusted under 35 U.S.C. 154(b) by 419 days.

(21) Appl. No.: 10/255,451

(22) Filed: Sep. 26, 2002

(65) Prior Publication Data

US 2004/0062790 A1    Apr. 1, 2004

(51) Int. Cl.
*A61F 2/00*     (2006.01)
*A61F 13/00*    (2006.01)

(52) U.S. Cl. .................. 424/426; 424/422; 424/423; 424/424; 424/426; 424/443; 424/449

(58) Field of Classification Search ........... 424/426, 424/422, 423
See application file for complete search history.

(56) References Cited

U.S. PATENT DOCUMENTS

| | | | |
|---|---|---|---|
| 4,439,420 A | | 3/1984 | Mattei et al. |
| 4,668,295 A | * | 5/1987 | Bajpai ................. 106/690 |
| 5,583,114 A | | 12/1996 | Barrows et al. |
| 5,595,735 A | * | 1/1997 | Saferstein et al. ....... 424/94.64 |
| 5,635,162 A | | 6/1997 | Fischer et al. |
| 5,681,873 A | * | 10/1997 | Norton et al. ............... 523/115 |
| 6,011,011 A | | 1/2000 | Hageman |
| 6,083,522 A | | 7/2000 | Chu et al. |
| 6,096,309 A | | 8/2000 | Prior et al. |
| 6,117,444 A | | 9/2000 | Orgill et al. |
| 6,294,287 B1 | | 9/2001 | Lee et al. |
| 6,420,454 B1 | | 7/2002 | Wenz et al. |
| 6,426,332 B1 | | 7/2002 | Rueger et al. |
| 6,458,147 B1 | | 10/2002 | Cruise et al. |
| 6,458,889 B1 | | 10/2002 | Trollsas |
| 6,534,491 B1 | | 3/2003 | Levin et al. |
| 6,566,345 B1 | | 5/2003 | Miller et al. |
| 6,624,245 B1 | | 9/2003 | Wallace et al. |
| 2002/0010150 A1 | | 1/2002 | Cortese et al. |
| 2003/0004568 A1 | | 1/2003 | Ken et al. |
| 2003/0104031 A1 | | 6/2003 | Dumont et al. |

FOREIGN PATENT DOCUMENTS

| | | |
|---|---|---|
| JP | 07 118157 A | 5/1995 |
| RU | 2 034 572 | 10/1995 |
| WO | WO 92/13495 | 8/1992 |
| WO | WO 01/97871 | 12/2001 |

OTHER PUBLICATIONS

Aanals of Surgery, vol. 132, pp. 1128-1130, "New Absorbable Hemostatic Bone Wax", Dr. Geary et al. 1950.*
Orgill et al "Polyethylene glycol/microfibrillar collagen compositive as a new resorbable hemostatic bone wax" J. Biomed Mater Res. Mar. 5, 1998; vol. 39 No. 3: pp. 358-363. (Abstract))
New synthetic absorbable polymers as BMP carriers: plastic properties of poly-D, L-tactic acid-polyethylene glycol block copolymers J. Biomed Mater Res. Oct. 1999; vol. 47 No. 1: pp. 104-110 (Abstract).
Orgill, et al. "Polyethylene glycol/microfibrilar collagen composite as a new resorbable hemostatic bone wax". J. Biomed Mater Res. Mar. 5, 1998;39(3) -Abstract.
Supplementary Partial European Search Report.

* cited by examiner

*Primary Examiner*—Thurman K. Page
*Assistant Examiner*—Isis Ghali
(74) *Attorney, Agent, or Firm*—William D. Schmidt; Kalow & Springut LLP

(57) ABSTRACT

The present invention provides methods and compositions involving resorbable hemostatic agents that have the essential absence of microfibrillar collagen. Resorbable hemostatic agents of the present invention comprise polyethylene glycol, which controls bleeding in tissue and does not delay or interfere with healing. The resorbable hemostatic agents of the present invention are biodegradable and biocompatible agents that effectively control bleeding in bone and other tissue without interfering with the subsequent healing of the tissue.

16 Claims, No Drawings

HEMOSTATIC COMPOSITIONS AND METHODS

BACKGROUND OF THE INVENTION

One of the major problems with medical or surgical procedures is excessive blood loss or hemorrhage. With the advent of topical hemostatic agents, control of blood loss during these procedures has greatly improved. In general, hemostatic agents provide rapid initiation of a hemostatic plug formed through platelet activation, aggregation, adhesion and gross clot formation. Additionally, ideal hemostatic agents should possess properties such as ease of application, bioresorption, and minimal or no antigenicity.

A wide variety of hemostatic agents are made from different base materials i.e., collagen, gelatin, oxidized regenerated cellulose, fibers, gauze sponges and fibrin. These agents are used in a wide variety of medical and surgical procedures. For example, microfibrillar collagen is used extensively for wide-area parenchyma bleeding and for laparoscopic procedures. Hemostatic sponges are used in surgical as well as dermatological applications where adherence to the wound site and ease of removal are important considerations.

When the damaged tissue is particularly dense (i.e., bone or cartilage), bone waxes are often employed for hemostasis especially where control of bleeding is needed. For example, bone wax is often used to control hemorrhages by closure of intra-osseous vessel canals in cardiac, orthopedic, dental, oral and maxofacial surgery. Typically, bone waxes possess desirable properties i.e., soft, moldable, easy to apply. However, conventional bone waxes interfere with bone healing and are not resorbed by adjacent bone or local surrounding tissues. Bone waxes may also induce inflammatory responses, promote infection and inhibit bone regeneration.

Thus, there is a need for compositions and methods that can easily be delivered to tissue (i.e., bone or cartilage) and control hemostasis or deliver bone growth stimulators (i.e., hydroxyapatite) and/or bone growth factors without delaying or inhibiting bone repair. There is also a need for effective resorbable hemostatic agents that are biodegradable, compatible with bone repair and are easily delivered to the damaged tissue.

SUMMARY OF THE INVENTION

The present invention provides compositions and methods involving resorbable hemostatic agents that are easily applied to the site of bleeding and control hemostasis without limiting or delaying the subsequent healing of the tissue. The resorbable hemostatic agents of the present invention are biodegradable, biocompatible hemostatic agents that effectively control bleeding in tissue i.e., bone, muscle, cartilage without interfering with healing of the tissue.

In one embodiment, the present invention provides a resorbable hemostatic agent having the essential absence of microfibrillar collagen comprising polyethylene glycol.

In another embodiment, the present invention provides a resorbable hemostatic agent having the essential absence of microfibrillar collagen comprising between about 70% to about 95% by weight high molecular weight polyethylene glycol and between about 1% to about 10% by weight low molecular weight polyethylene glycol; and a bone growth stimulator which comprises calcium, hydroxyapatite or tricalcium phosphate.

In still another embodiment, the present invention provides a method for treating defects in dense tissue, comprising application to the defect of a resorbable hemostatic agent having the essential absence of microfibrillar collagen, the hemostatic agent being comprised of polyethylene glycol.

In yet another embodiment, the present invention provides a method for promoting bone growth in a mammal in need of bone repair, comprising applying to the bone a resorbable hemostatic agent having the essential absence of microfibrillar collagen, the resorbable hemostatic agent comprising between about 70% to about 95% by weight high molecular weight polyethylene glycol and between about 1% to about 10% by weight low molecular weight polyethylene glycol; the hemostatic agent having a bone growth stimulator which comprises calcium, hydroxyapatite, tricalcium phosphate, bone growth factors such as bone morphogenic proteins or combinations thereof.

For a better understanding of the present invention together with other and further advantages and embodiments, reference is made to the following description taken in conjunction with the examples, the scope of which is set forth in the appended claims.

DETAILED DESCRIPTION OF THE INVENTION

The invention will now be described in connection with preferred embodiments. These embodiments are presented to aid in an understanding of the present invention and are not intended to, and should not be construed to, limit the invention in any way. All alternatives, modifications and equivalents, which may become obvious to those of ordinary skill on reading this disclosure are included within the spirit and scope of the present invention.

This disclosure is not a primer on the manufacture of hemostatic agents and methods of using them, basic concepts known to those skilled in the art have not been set forth in detail.

The invention includes a resorbable hemostatic agent having the essential absence of microfibrillar collagen. Hemostatic agents of the present invention include compositions that control blood loss and provide rapid initiation of hemostatic plug formation through tamponade, platelet activation, platelet adhesion, and/or gross blood coagulation. Hemostatic agents of the present invention may include adjuvants such as preservatives, wetting agents, emulsifying agents, and dispersing agents. The hemostatic agents of the present invention may prevent the action of microorganisms by inclusion of various antibacterial and antifungal agents, for example, paraben, chlorobutanol, phenol sorbic acid, and the like.

Preferably, the hemostatic agent is sterile before use and is in a solid, semisolid or liquid form at temperatures ranging from about 0° C. to about 45° C. As used herein, the term "semi-solid" is intended to encompass viscous states ranging from a liquid to a stiff paste. The ability of the hemostatic agent to change viscosity at varying temperatures allows for uncomplicated application of the hemostatic agent in a malleable, semi-solid form to the wound. Upon application to the wound, the resorbable agent is subjected to elevated body temperature, which causes the hemostatic agent to become less viscous. In less viscous form, the agent is quickly reabsorbed into adjacent bone and surrounding body tissue. Unlike conventional hemostatic agents i.e., bone wax, the hemostatic agent of the present invention has a limited presence at the wound site and does not inhibit tissue growth.

The present invention includes a resorbable hemostatic agent having the essential absence of microfibrillar collagen. The phrase "essential absence of microfibrillar collagen", is an art recognized phrase and is intended to mean that the hemostatic agent does not contain exogenous microfibrillar collagen. Exogenous microfibrillar collagen is described for example in U.S. Pat. No. 6,117,444. This entire disclosure is herein incorporated by reference into the present disclosure.

The resorbable hemostatic agents of the present invention comprise polyethylene glycol (PEG). The polyethylene glycol of the present invention is water soluble, preferably, biocompatible, and has the ability to change from solid to liquid form at increased temperatures. Typically, polyethylene glycol is reabsorbed within several hours after the application of the hemostatic agent to bleeding tissue. Since the polyethylene glycol is rapidly removed, the resorbable hemostatic agent allows for fresh blood and macrophages to infiltrate the wound site. Preferably, the resorbable hemostatic agent comprises from about 65% to up to 100% by weight of PEG, more preferably, from about 70% to up to 100% by weight PEG. The preferred formulation comprises about 90% PEG 1450 and 10% PEG 400.

In a preferred embodiment, high molecular weight and low molecular weight polyethylene glycols are used. By combining low molecular weight polyethylene glycol, which is in liquid form at room temperature, with high molecular weight polyethylene glycol, which is a solid at room temperature, the hemostatic agent takes on a malleable consistency. Preferably, the resorbable hemostatic agent comprises about 90%–91% by weight high molecular weight polyethylene glycol and about 9% to about 10% by weight low molecular weight polyethylene glycol. However, the consistency of the resorbable hemostatic agent can be adjusted by varying the percentages of high molecular weight and low molecular weight polyethylene glycol. The percentages of high molecular weight polyethylene glycol in the resorbable hemostatic agent can range from about 70% to about 95% by weight. The low molecular weight polyethylene glycol can comprise about 5% to about 30% by weight of the resorbable agent.

Polyethylene glycol suitable for use in the present invention includes, but is not limited to, various low molecular weight polyethylene glycols and various high molecular weight polyethylene glycols of various consistency. Low molecular weight polyethylene glycols can include, for example, polyethylene glycol with an average molecular weight ranging from about 300 to about 600. The high molecular weight polyethylene glycols, for example, can include polyethylene glycol with an average molecular weight ranging from about 1000 to about 4000. Preferably, PEG 400 and PEG 1450 are used in combination. Polyethylene glycol of the described molecular weight is available from J. T. Baker.

The resorbable hemostatic agent of the present invention can further be used as a plug for the treatment of wounds in dense tissues, such as bone, muscle and/or cartilage. For example, bleeding from puncture wounds in skeletal muscle can be stopped by filling the wound with the resorbable hemostatic agent. In addition, the viscosity of the resorbable hemostatic agent can be adjusted for treatments in which the body is exposed to elevated or reduced temperatures. For example, during cardiopulmonary bypass surgery, the body temperature is lowered to reduce the heart rate. By increasing the proportion of low molecular weight polyethylene glycol and reducing the proportion of high molecular weight polyethylene glycol, a less viscous hemostatic "plug" can be easily applied to the cold tissue. After the procedure, as the body temperature returns to normal, the polyethylene glycol is rapidly reabsorbed by the aqueous nature of the surrounding tissue. Although it is not intended to be limited to any one particular theory, it is believed that the surrounding tissue contains water that mixes with the polyethylene glycol and allows resorption to occur.

In one embodiment of the present invention, the hemostatic agent provides a high surface to volume ratio with the damaged tissue. This allows greater contact with the wound resulting in enhanced hemostasis, while eliciting minimal or no inflammatory response.

In another embodiment of the present invention, the resorbable hemostatic agent includes a biologically active healing adjunct or bone growth stimulator or regenerating substance to further aid in the process of bone repair. The term "healing adjunct", as used herein, refers to biologically active substances, such as antibiotics and anti-inflammatory agents that aid in preventing infection or inflammatory response.

Antimicrobial agents used in the hemostatic agent can be any known in the art. Suitable antimicrobial agents include, but are not limited to, streptomycin, tetracycline, penicillin, vancomycin, clindamycin, erythromycin, polymyxin, bacitracin, ciprofloxacin, ofloxacin, levofloxacin, rifampin, gentamicin, cefazolin, oxacillin, ampicillin, silver, silversulfadiazine and the like.

Anti-inflammatory agents used in the hemostatic composition can be any known in the art. Anti-inflammatory agents include, but are not limited to, ibuprofen, naproxen, aspirin, celecoxib, diclofenac, etodolac, fenoprofen, indomethacin, ketoprofen, ketorolac, oxaprozin, nabumetone, sulindac, tolmetin, rofecoxib, and the like.

In another embodiment of the present invention, the resorbable hemostatic agent includes a bone growth stimulator. Suitable bone growth stimulators include substances that can enhance bone repair. Some examples of bone growth stimulators include, but are not limited to, calcium, hydroxyapatite, tricalcium phosphate, chitosan, coral derivatives, bone growth factors, such as for example bone morphogenic proteins, and the like. Hydroxyapatite includes $Ca_{10}(PO_4)_6(OH)_2$, and is exogenous calcium phosphate that resembles the primary inorganic component of bone. This agent provides an osteophillic matrix for bone to bond and grow.

Tricalcium phosphate includes $Ca_3(PO_4)_2$, bone ash, alpha or beta tricalcium phosphate, and combinations thereof. This agent is important in bone regeneration in vivo.

Coral derivatives include bone substitutes derived from natural coral. Typically, coral derivatives contain hydroxyapatite. A preferred powdered coral derivative suitable for use in the present invention is ProOsteon 500 R.

Bone morphogenic proteins (BMPs) is an art recognized term and includes proteins from the transforming growth factor beta (TGF β) superfamily that regulate growth and differentiation of a variety of cell types in diverse tissues. BMPs have the ability to stimulate bone growth. Preferred BMPs suitable for use in the present invention include BMP-2, BMP-7, MP-52, and the like.

In the most preferred embodiment, the present invention provides a method for promoting bone growth in a mammal in need of bone repair, comprising applying to the bone a resorbable hemostatic agent having the essential absence of microfibrillar collagen, the resorbable hemostatic agent comprising between about 70% to about 95% by weight high molecular weight polyethylene glycol and between about 1% to about 30% by weight low molecular weight polyethylene glycol; the hemostatic agent having a bone growth stimulator which comprises calcium hydoxylapatite or tricalcium phosphate.

The hemostatic agents of the present invention can be applied to the defective tissue. Applying the hemostatic agent includes administering the agent to the muscle, skin, bone, cartilage, mucosa membrane, or any surface that requires hemostasis. Tissues, as used herein, are an aggregation of similarly specialized cells, which together perform certain special functions. Tissue defects include wounds, breaks, fractures, scars, and unwanted gaps.

The above compositions and methods of the present invention can be used in vivo, in vitro, and ex vivo, for example, in living mammals as well as in cultured tissue, organ or cellular systems. Mammals include, for example, humans, as well as pet animals such as dogs and cats, laboratory animals, such as rats and mice, hamsters and farm animals, such as horses and cows.

Having now generally described the invention, the same may be more readily understood through the following reference to the following examples, which are provided by way of illustration and are not intended to limit the present invention unless specified.

EXAMPLES

The Examples below are contemplated. These examples will show that hemostatic agents comprising polyethylene glycol are at least as effective as hemostatic agents comprising beeswax as well as microfibrillar collagen.

Example 1

Bone Wax Formulation #1

| Component | % w/w |
|---|---|
| PEG 1450 | 90 |
| PEG 400 | 10 |

This resorbable formulation has very similar physical handling properties, density and orthopedic hemostasis performance to that of the insoluble beeswax formulation currently available. The comparative performance to this formulation containing collagen would be negligible. Orgill reported that bone healing when treated with this formulation containing microfibrillar collagen was not different from those sites left untreated. See Orgill et al., *J. Biomed. Mater. Res.* 39: 358–63 (1998).

Example 2

Bone Wax Formulation #2

| Component | Gm |
|---|---|
| PEG 1450 + PEG 400 | 99 |
| Hydroxyapatite or Tricalcium Phosphate | 1 |

This formulation provides the bone growth stimulator hydroxyapatite or tricalcium phosphate.

Example 3

Bone Wax Formulation #3

| Component | gm |
|---|---|
| PEG 1450 + PEG 400 | 99 |
| silversulfadiazine | 1 |

The formulation above may also include Bone Morphogenic Proteins (BMP) or other biological modifiers.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to essential features hereinbefore set forth and as follows in the scope of the appended claims.

What is claimed is:

1. A resorbable hemostatic agent that does not contain microfibrillar collagen, the resorbable hemostatic agent consisting of polyethylene glycol, the polyethylene glycol consisting of from about 90% to about 95% by weight of high molecular weight to polyethylene glycol having an average molecular weight ranging from about 1000 to about 4000 and about 1% to about 10% by weight of low molecular weight polyethylene glycol having an average molecular weight ranging from about 300 to about 600 and optionally at least one of a bone growth stimulator, antimicrobial or anti-inflammatory drug.

2. A resorbable hemostatic agent according to claim 1, wherein the bone growth stimulator is calcium hydroxyapatite or tricalcium phosphate.

3. A resorbable hemostatic agent according to claim 1, wherein the antimicrobial is selected from a group consisting of streptomycin, tetracycline, penicillin, vancomycin, clindamycin, erythromycin, polymyxin, bacitracin, ciprofloxacin, rifampin, gentamicin, cefazolin, oxacillin, silversulfadiazine, and ampicillin.

4. A resorbable hemostatic agent that does not contain microfibrillar collagen consisting of between about 90% to about 95% by weight of high molecular weight polyethylene glycol having an average molecular weight ranging from about 1000 to about 4000 and between about 1% to about 10% by weight of low molecular weight polyethylene glycol having an average molecular weight ranging from about 300 to about 600; a bone growth stimulator selected from the group consisting of hydroxyapatite, tricalcium phosphate or bone growth factor, and optionally at least one antimicrobial or anti-inflammatory drug.

5. A resorbable hemostatic agent according to claim 4, wherein the antimicrobial is selected from a group consisting of streptomycin, tetracycline, penicillin, vancomycin, clindamycin, erythromycin, polymyxin, bacitracin, ciprofloxacin, rifampin, gentamicin, cefazolin, oxacillin, silversulfadiazine and ampicillin.

6. A method for treating defects in dense tissue, comprising applying to the defect a resorbable hemostatic agent that does not contain microfibrillar collagen, the hemostatic agent consisting of from about 90% to about 95% by weight high molecular weight polyethylene glycol having an average molecular weight ranging from about 1000 to about 4000 and between about 1% to about 10% by weight low molecular weight polyethylene glycol having an average molecular weight ranging from about 300 to about 600.

7. A method according to claim 6, wherein the dense tissue is muscle, cartilage or bone.

8. A method for promoting bone growth in a mammal in need of bone repair, comprising applying to the bone a resorbable hemostatic agent that does not contain microfibrillar collagen, the resorbable hemostatic agent consisting 01 between about 90% to about 95% by weight high molecular weight polyethylene glycol having an average molecular weight ranging from about 1000 to about 4000 and between about 1% to about 10% by weight low molecular weight polyethylene glycol having an average molecular weight ranging from about 300 to about 600 and a bone growth stimulator selected from the group consisting of hydroxyapatite or tricalcium phosphate.

9. A resorbable hemostatic agent according to claim 1, wherein the polyethylene glycol is polyethylene glycol 1450 and polyethylene glycol 400.

10. A resorbable hemostatic agent according to claim 4, wherein the polyethylene glycol is polyethylene glycol 1450 and polyethylene glycol 400.

11. A method according to claim 6, wherein the polyethylene glycol is polyethylene glycol 1450 and polyethylene glycol 400.

12. A resorbable hemostatic agent composition, consisting of between 70% to about 95% by weight of high molecular weight polyethylene glycol having an average molecular weight ranging from about 1000 to about 4000 and about 1% to 30% by weight of low molecular weight polyethylene glycol having an average molecular weight ranging from about 300 to about 600 and optionally at least one of a bone growth stimulator, antimicrobial or anti-inflammatory drug.

13. A resorbable hemostatic agent composition according to claim 12, wherein the polyethylene glycol is polyethylene glycol 1450 and polyethylene glycol 400.

14. A resorbable hemostatic agent composition according to claim 12, wherein the bone growth stimulator is calcium hydroxyapatite or tricalcium phosphate.

15. A resorbable hemostatic agent composition according to claim 12, wherein the antimicrobial is selected from a group consisting of streptomycin, tetracycline, penicillin, vancomycin, clindamycin, erythromycin, polymyxin, bacitracin, ciprofloxacin, rifampin, gentamicin, cefazolin, oxacillin, silversulfadiazine, and ampicillin.

16. A resorbable hemostatic agent composition consisting of about 90% to about 95% by weight of high molecular weight polyethylene glycol having an average molecular weight ranging from about 1000 to about 4000 and about 1% to 10% by weight of low molecular weight polyethylene glycol having an average molecular weight ranging from about 300 to about 600.

* * * * *